US012735708B2

(12) United States Patent
Zhang et al.

(10) Patent No.: US 12,735,708 B2
(45) Date of Patent: Sep. 15, 2026

(54) ENGINEERED EXOSOME FOR TREATING HYPERTROPHIC SCAR (HTS), AND PREPARATION METHOD AND USE THEREOF

(71) Applicant: CHINESE PLA GENERAL HOSPITAL, Beijing (CN)

(72) Inventors: Cuiping Zhang, Beijing (CN); Sheng Meng, Beijing (CN); Kui Ma, Beijing (CN); Xi Liu, Beijing (CN); Xiaobing Fu, Beijing (CN)

(73) Assignee: CHINESE PLA GENERAL HOSPITAL, Beijing (CN)

( * ) Notice: Subject to any disclaimer, the term of this patent is extended or adjusted under 35 U.S.C. 154(b) by 192 days.

(21) Appl. No.: 18/603,433

(22) Filed: Mar. 13, 2024

(65) Prior Publication Data

US 2025/0002911 A1 Jan. 2, 2025

(30) Foreign Application Priority Data

Jun. 30, 2023 (CN) ......................... 202310793039.2

(51) Int. Cl.

| | |
|---|---|
| ***C12N 15/113*** | (2010.01) |
| ***A61K 9/50*** | (2006.01) |
| ***A61K 31/7105*** | (2006.01) |
| ***A61P 17/00*** | (2006.01) |
| ***C12N 5/0775*** | (2010.01) |
| ***C12N 15/86*** | (2006.01) |

(52) U.S. Cl.

CPC .......... *C12N 15/113* (2013.01); *A61K 9/5068* (2013.01); *A61K 31/7105* (2013.01); *A61P 17/00* (2018.01); *C12N 5/0662* (2013.01); *C12N 15/86* (2013.01); *C12N 2310/141* (2013.01); *C12N 2510/02* (2013.01); *C12N 2740/15043* (2013.01)

(58) Field of Classification Search

None

See application file for complete search history.

(56) References Cited

PUBLICATIONS

Liu et al., Frontiers in Immunology (2023), 14, DOI 10.3389/fimmu.2023.1109381 (9 pages).*

Zhou et al., Acta Biochem. Biophys. Sin. (2021), 53(8), pp. 1106-1108.*

Gao et al., Frontiers in Bioengineering and Biotechnology (2023), 10, DOI 10.3389/fbioe.2022.1100892 (17 pages).*

* cited by examiner

*Primary Examiner* — Brian J Davis

(74) *Attorney, Agent, or Firm* — David R. Stevens; Stevens Law Group

(57) ABSTRACT

The present disclosure belongs to the technical fields of genetic engineering and biotherapeutic drugs, and relates to an engineered exosome for treating hypertrophic scar (HTS), and a preparation method and use thereof. In the present disclosure, the engineered exosome for treating HTS is a mesenchymal stem cell (MSC)-derived exosome over-expressing miR-141-3p. The exosome can significantly reduce formation of the HTS.

6 Claims, 6 Drawing Sheets

Specification includes a Sequence Listing.

miR-141$^{NC}$-Exos miR-141$^{OE}$-Exos

```
                          SEQUENCE LISTING


Sequence total quantity: 2
SEQ ID NO: 1             moltype = DNA  length = 22
FEATURE                  Location/Qualifiers
misc_feature             1..22
                         note = lentivirus overexpressing miR-141-3p
source                   1..22
                         mol_type = other DNA
                         organism = synthetic construct
SEQUENCE: 1
taacactgtc tggtaaagat gg                                           22

SEQ ID NO: 2             moltype = DNA  length = 19
FEATURE                  Location/Qualifiers
misc_feature             1..19
                         note = lentivirus LV3-NC
source                   1..19
                         mol_type = other DNA
                         organism = synthetic construct
SEQUENCE: 2
ttctccgaac gtgtcacgt                                               19
```

ENGINEERED EXOSOME FOR TREATING HYPERTROPHIC SCAR (HTS), AND PREPARATION METHOD AND USE THEREOF

CROSS REFERENCE TO RELATED APPLICATION

This patent application claims the benefit and priority of Chinese Patent Application No. 2023107930392, filed with the China National Intellectual Property Administration on Jun. 30, 2023, the disclosure of which is incorporated by reference herein in its entirety as part of the present application.

REFERENCE TO SEQUENCE LISTING

A computer readable XML file entitled "GWP20231209922-sequence listing", which was created on Dec. 30, 2025 and has a file size of about 3,713 bytes, contains the sequence listing for this application and is hereby incorporated by reference in its entirety.

TECHNICAL FIELD

The present disclosure belongs to the technical fields of genetic engineering and biotherapeutic drugs, and specifically relates to an engineered exosome for treating hypertrophic scar (HTS), and a preparation method and use thereof.

BACKGROUND

Exosomes are regarded as a carrier that mediates communication between cells through paracellular secretion. Exosomes as nanoscale extracellular vesicles with a double-layer membrane structure contain a variety of active ingredients such as proteins, DNAs, mRNAs, and non-coding RNAs, and can be taken up by other cells to affect the biological functions of other cells. Therefore, in the field of exosome-based therapy, the exosomes can be used as a carrier of drugs or therapeutic molecules to transport their contents into target cells and regulate the biological functions of target cells to achieve therapeutic purposes. However, there is currently a lack of exosomes that can be used to treat hypertrophic scars (HTS).

SUMMARY

A purpose of the present disclosure is to provide an engineered exosome for treating hypertrophic scar (HTS), and a preparation method and use thereof. The exosome can significantly inhibit formation of the HTS.

The present disclosure provides an engineered exosome for treating HTS, where the engineered exosome is a mesenchymal stem cell (MSC)-derived exosome overexpressing miR-141-3p.

The present disclosure further provides a preparation method of the engineered exosome for treating HTS, including the following steps:

infecting an MSC with a miR-141-3p-overexpressing lentivirus, and conducting screening to obtain a stably transduced cell line; and subjecting the stably transfected cell line to multiplication culture, and conducting exosome extraction to obtain the engineered exosome for treating HTS.

Preferably, the miR-141-3p-overexpression lentivirus is packaged by an LV3 vector.

Preferably, the infecting is conducted for 20 h to 24 h.

Preferably, the screening includes screening a successfully transfected MSC with puromycin.

Preferably, a medium for the multiplication culture includes a special serum-free medium for the MSC.

Preferably, a process of the exosome extraction includes the following steps:

collecting a cell supernatant obtained from the multiplication culture, subjecting the cell supernatant to low-speed centrifugation, collecting a resulting supernatant to allow filtration with an ultrafiltration membrane, subjecting a resulting filtrate to ultracentrifugation, and collecting a resulting precipitate to obtain the engineered exosome for treating HTS.

Preferably, the low-speed centrifugation is conducted at 2,000 g for 10 min; and the ultrafiltration membrane has a pore size of 0.22 μm.

Preferably, the ultracentrifugation is conducted at 100,000 g for 75 min.

The present disclosure further provides use of the engineered exosome for treating HTS or an engineered exosome for treating HTS prepared by the preparation method in preparation of a drug for treating HTS.

The present disclosure provides an engineered exosome for treating HTS. The engineered exosome can overexpress miR-141-3p to significantly inhibit formation of the HTS. The exosome of the present disclosure can load more miR-141-3p and transport same to scar tissues, acting on cells in the wound tissue to better exert specific regulatory effects and inhibit the HTS. Moreover, the exosome shows stable quality, no tissue rejection, and no toxicity, are suitable for large-scale extraction, and have a strong potential value in clinical applications. This provides a new strategy for future treatment of patients with post-traumatic HTS.

BRIEF DESCRIPTION OF THE DRAWINGS

To describe the technical solutions in embodiments of the present disclosure or in the prior art more clearly, the accompanying drawings required in the embodiments are briefly described below. Apparently, the accompanying drawings in the following description show merely some embodiments of the present disclosure, and other drawings can be derived from these accompanying drawings by those of ordinary skill in the art without creative efforts.

DETAILED DESCRIPTION OF THE EMBODIMENTS

Figure 1A:
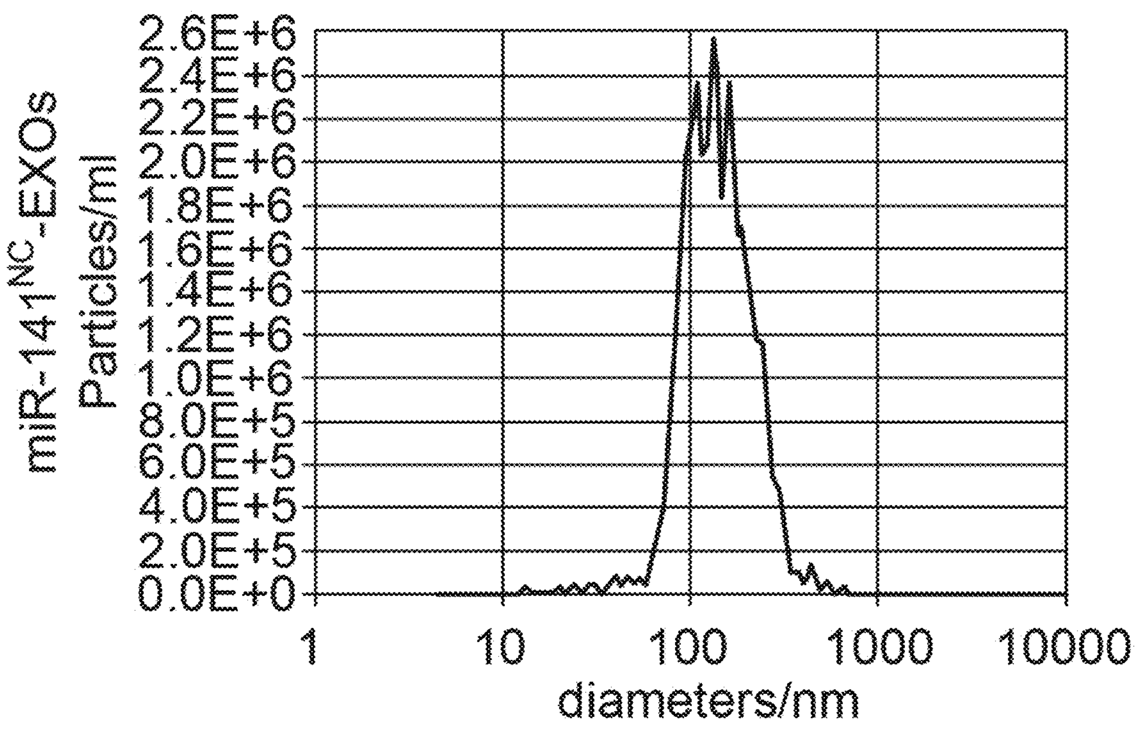
FIGS. 1A-B show nanoparticle analysis diagram of the engineered MSC-derived exosome provided in Example 2 of the present disclosure.

The present disclosure provides an engineered exosome for treating HTS, where the engineered exosome is a mesenchymal stem cell (MSC)-derived exosome overexpressing miR-141-3p. In the present disclosure, the engineered exosome can act on cells in wound tissue and can efficiently exert specific regulatory effects and inhibit HTS. Moreover, the engineered exosome shows stable quality, no tissue rejection, and non-toxicity, are suitable for large-scale extraction, and has a strong potential value in clinical applications.

The present disclosure further provides a preparation method of the engineered exosome for treating HTS, including the following steps:

infecting an MSC with a miR-141-3p-overexpressing lentivirus, and conducting screening to obtain a stably transduced cell line; and subjecting the stably transfected cell line to multiplication culture, and conducting exosome extraction to obtain the engineered exosome for treating HTS.

In the present disclosure, an MSC is infected with a miR-141-3p-overexpressing lentivirus, and screening is conducted to obtain a stably transduced cell line. The miR-141-3p-overexpression lentivirus is preferably packaged by an LV3 vector. The LV3 vector is preferably an LV3 (H1/GFP&Puro, GenePharma) vector. The infecting is conducted for preferably 20 h to 24 h. The MSC is preferably a human adipose-derived mesenchymal stem cell (hAD-MSC). Genetic engineering editing makes the exosome overexpress miR-141-3p more effective in treating HTS. The screening includes screening a successfully transfected MSC with puromycin. Specifically, the screening preferably includes drug screening using a medium containing the puromycin. Preferably, a cell line stably expressing miR-141-3p is obtained after 2 weeks of screening.

In the present disclosure, the stably transfected cell line is subjected to multiplication culture. A medium for the multiplication culture includes preferably a special serum-free medium for the MSC.

In the present disclosure, an exosome is extracted to obtain the engineered exosome for treating HTS after the multiplication culture is completed. Preferably, a process of the exosome extraction includes the following steps: collecting a cell supernatant obtained from the multiplication culture, subjecting the cell supernatant to low-speed centrifugation, collecting a resulting supernatant to allow filtration with an ultrafiltration membrane, subjecting a resulting filtrate to ultracentrifugation, and collecting a resulting precipitate to obtain the engineered exosome for treating HTS.

In the present disclosure, the low-speed centrifugation is conducted at preferably 2000 g for preferably 10 min. The low-speed centrifugation removes macromolecular substances. The ultrafiltration membrane has a pore size of preferably 0.22 μm, since the ultrafiltration membrane with the pore size can remove various impurities, suspended particles, sediments, and microorganisms (bacteria and viruses) in the cell supernatant, providing reliable filtration and sterilization for subsequent exosome acquisition. The ultracentrifugation is conducted preferably 100,000 g for preferably 75 min. After collecting the precipitate, the precipitate is preferably washed. The washing preferably includes resuspension and centrifugation. Specifically, the resuspension is preferably conducted using sterile PBS. The centrifugation is preferably conducted at 100,000 g for 75 min. After centrifugation, the resulting precipitate is the washed exosome.

In the present disclosure, the preparation method is different from electrotransfection and other methods, and can better maintain the integrity of exosomes while up-regulating the utility molecules within same. MSCs are transfected with lentivirus overexpressing miR-141-3p, such that the extracted exosomes can load more utility molecules (miR-141-3p) and increase the content of active ingredients in exosomes. The same dose of exosomes exerts a stronger therapeutic effect and specifically inhibits the formation of HTS. On the other hand, the method for extracting exosomes is simple and suitable for large-scale production, and the obtained exosomes have desirable biocompatibility. Therefore, the present disclosure has a broad prospect in clinical applications and provides a novel strategy for treating HTS.

The present disclosure further provides use of the engineered exosome for treating HTS or an engineered exosome for treating HTS prepared by the preparation method in preparation of a drug for treating HTS.

In the present disclosure, the engineered exosome is preferably identified before the use. The identification preferably includes the following steps:

(1) detecting a concentration and a particle size of the exosome using a nanoparticle analysis system;
(2) observing an appearance of the exosome with TEM, and conducting photographing and recording;
(3) extracting a total protein of the exosome, and detecting surface specific markers of the exosome: CD63, CD9, TSG101, and Calnexin through a Western blot experiment; and
(4) extracting a total RNA of the exosome, and detecting changes in an expression level of miR-141-3p in the engineered exosome by qRT-PCR.

In the present disclosure, an exosome is selected with mean and peak particle size distribution concentrated in the range of 50 nm to 150 nm, a double-layer film-like structure under TEM, an overall appearance being spherical or cup-shaped, and expressing CD63, CD9, and TSG101 but not Calnexin for subsequent applications.

In order to further illustrate the present disclosure, the engineered exosome for treating HTS, and the preparation method and the use thereof provided by the present disclosure are described in detail below with reference to the accompanying drawings and examples, but the accompanying drawings and the examples should not be construed as limiting the protection scope of the present disclosure.

Example 1

An Engineered Exosome Overexpressing miR-141-3p Could be Used to Treat HTS.

A lentivirus overexpressing miR-141-3p (Sequence: 5'-TAACACTGTCTGGTAAAGATGG-3', SEQ ID NO: 1) was packaged and constructed using an LV3 (H1/GFP&Puro, GenePharma) vector commissioned by GenePharma Company.

The lentivirus was added to an MSC-specific serum-free medium (Youkang, China) to transfect hAD-MSC (Cell Bank of the Chinese Academy of Sciences). After 48 h, the medium was replaced with an MSC-specific serum-free medium containing puromycin to allow drug screening and culture. A cell line stably expressing miR-141-3p was obtained 2 weeks later.

The stably transduced cell line was subjected to multiplication culture in the MSC-specific serum-free medium.

When the cells grew to about 80% cell confluence, a collected cell supernatant was centrifuged at 2,000 g for 10 min at low speed to remove macromolecular substances such as cell debris and dead cells, and a resulting supernatant was continued to be collected.

The supernatant was filtered through an ultrafiltration membrane with a thickness of 0.22 μm, a filtrate was collected to allow ultracentrifugation at 100,000 g for 75 min, and a resulting supernatant was discarded. The exosomes were resuspended in sterile PBS to allow ultracentrifugation again at 100,000 g for 75 min. A resulting precipitate was resuspended in sterile PBS, which was the exosome preparation. The exosome preparation could be used immediately or frozen for later use.

Example 2

Figure 1B:
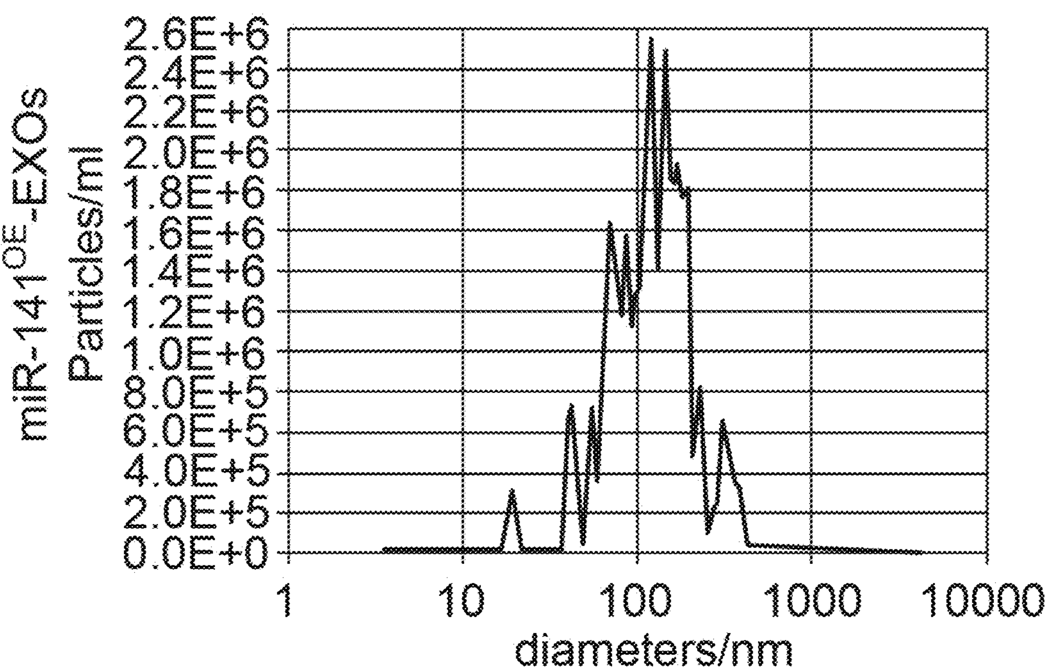

Identification of the Exosome Preparation Obtained in Example 1:

(1) The concentration and particle size of the exosome was detected with a nanoparticle analysis system, in which the exosome in the control group was named miR-141-$3p^{NC}$-Exos (a preparation process of the exosome included using the lentivirus LV3-NC (sequence 5'-TTCTCCGAACGTGTCACGT-3', SEQ ID NO: 2) controlled by miR-141-3p to allow transfection, and the remaining operations were the same as those in Example 1), while the exosome overexpressing miR-141-3p was named miR-141-$3p^{OE}$-Exos. The results were shown in FIGS. 1A-B (nanoparticle analysis chart of engineered MSC-derived exosomes, where a left picture showed NTA detection results of the miR-141-$3p^{NC}$-Exos group, and a right picture showed NTA detection results of the miR-141-$3p^{OE}$-Exos group). As shown in FIGS. 1A-B, the mean and peak particle sizes of the two groups of engineered exosomes were both concentrated in the range of 50 nm to 150 nm. There was no significant difference between the two groups, indicating that the results were consistent with the particle size distribution characteristics of exosomes.

Figure 2A:
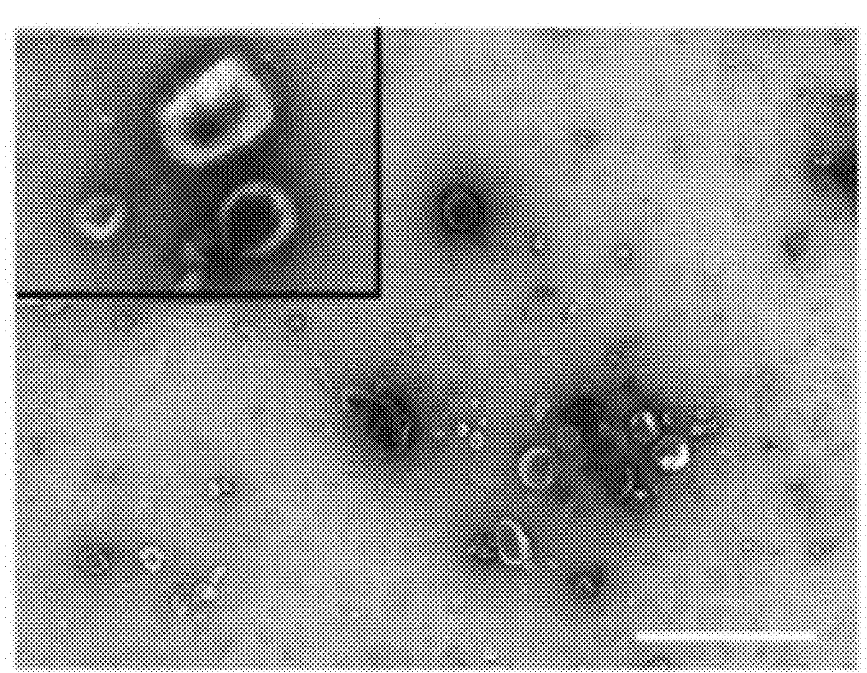
FIGS. 2A-B show transmission electron microscopy (TEM) image of the engineered MSC-derived exosome provided in Example 2 of the present disclosure.
Figure 2B:
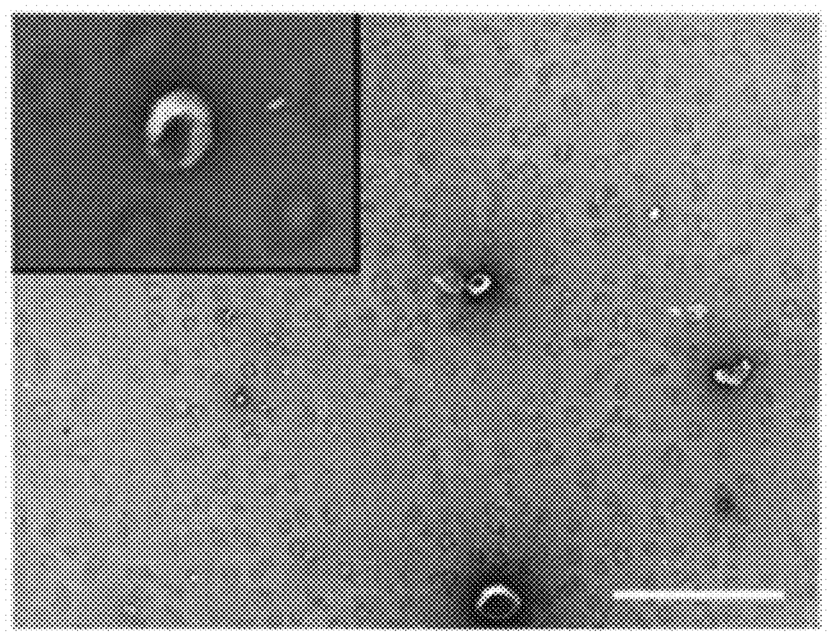

(2) The appearance of the exosomes was observed, photographed, and recorded by TEM. The results were shown in FIGS. 2A-B (TEM images of engineered MSC-derived exosomes, where a left image showed a TEM view of the miR-141-$3p^{OE}$-Exos group, and a right image showed a TEM view of the miR-141-$3p^{NC}$-Exos group). As shown in FIGS. 2A-B, both groups of exosomes had a classic double-layer membrane-like structure of exosomes, and their overall appearances were spherical or cup-shaped. There was also no significant difference in diameter between the two groups.

Figure 3:
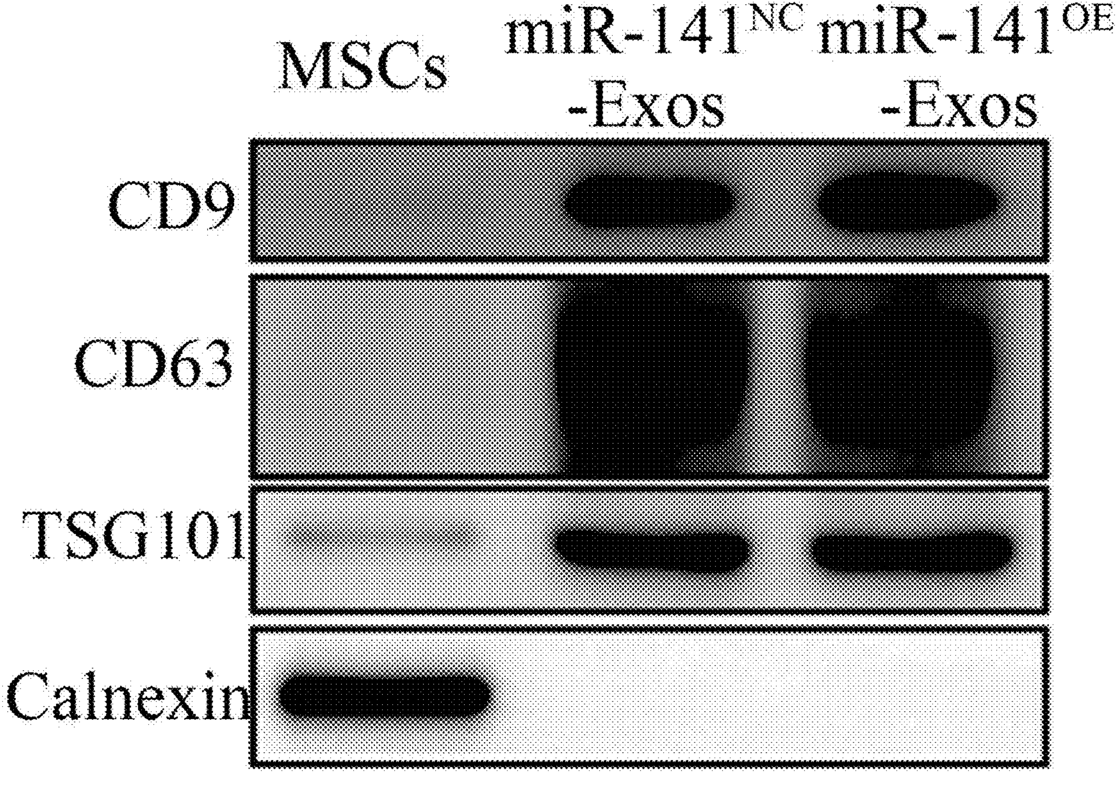
FIG. 3 shows the expression of surface-specific marker proteins of the engineered MSC-derived exosome provided in Example 2 of the present disclosure.

(3) The total proteins were extracted from hAD-MSCs, miR-141-$3p^{NC}$-Exos, and miR-141-$3p^{OE}$-Exos, a protein concentration was detected separately using a BCA kit, and Western blot experiments were conducted. A 10% concentration gel was prepared, samples were loaded on the gel to allow protein electrophoresis, transfer, blocking, and incubation with primary and secondary antibodies in sequence, and then exposure and photography were conducted by chemiluminescence imaging analysis to detect the expression levels of exosome surface-specific marker proteins such as CD63, CD9, and TSG101 as well as cell marker protein Calnexin in the cell lysis protein (Cell lysis group) of hAD-MSCs and engineered exosomes. The results were shown in FIG. 3 (results of expression of surface-specific marker proteins of engineered MSC-derived exosomes). As shown in FIG. 3, both miR-141-$3p^{NC}$-Exos and miR-141-$3p^{OE}$-Exos expressed the exosome marker proteins CD63, CD9, and TSG101, while the Calnexin was expressed in the hAD-MSCs group, indicating that the experiment was conducted correctly. This proved that the extracted miR-141-$3p^{NC}$-Exos and miR-141-$3p^{OE}$-Exos belonged to exosomes.

Figure 4:
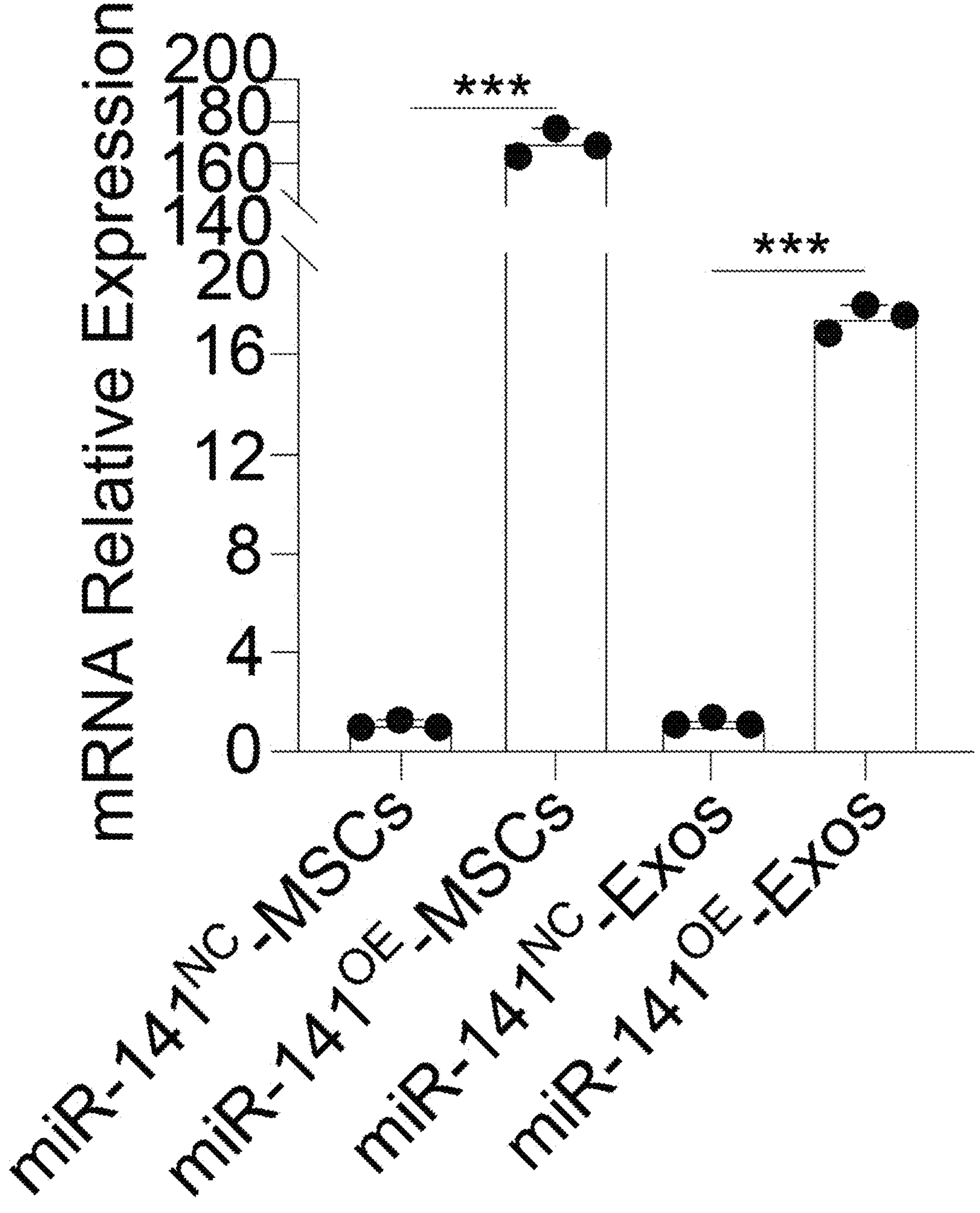
FIG. 4 shows expression levels of the MSCs provided in Example 2 of the present disclosure, MSCs transfected with a lentivirus vector overexpressing miR-141-3p, and the corresponding miR-141-3p in the exosome.

(4) After extracting the total RNA of the engineered exosome, an expression level of miR-141-3p in the engineered exosome was detected by qRT-PCR. The results were shown in FIG. 4 (expression levels of the MSCs, MSCs transfected with a lentivirus vector overexpressing miR-141-3p, and the corresponding miR-141-3p in exosomes). As shown in FIG. 4, after miR-141-$3p^{OE}$-Exos was compared with miR-141-$3p^{NC}$-Exos in the control group, miR-141-3p was highly expressed in miR-141-$3p^{OE}$-Exos. There was a statistically significant difference ($P<0.001$). It was suggested that the miR-141-3p could be loaded into exosomes.

Example 3

This example was based on the operating method described in Example 1. After completing Example 2 and passing the qualification (an exosome with mean and peak particle size distribution concentrated in the range of 50 nm to 150 nm, a double-layer film-like structure under TEM, an overall appearance being spherical or cup-shaped, and expressing CD63, CD9, and TSG101 but not Calnexin), a controlled trial of the engineered exosome preparation for the treatment of HTS on rabbit ears was conducted. A specific process included the following steps:

Establishment of the rabbit ear HTS model: 12 healthy New Zealand white rabbits (purchased from Beijing Keyu Animal Breeding Center) with the same gender and similar weight of 2 kg to 2.5 kg were randomly divided into four groups, with 3 rabbits in each group. Each rabbit carried 8 scar lesions, such that each group had 24 scar lesions, that is, each group of the present disclosure had conducted 24 repeated experiments (there were 4 observation time points, each time point having 6 repetitions). The rabbit was anesthetized with intramuscular injection of Lumeiling, and its ears were depilated using electric clippers. On a sterile towel, 4 circular wounds with a diameter of approximately 10 mm were made on the ventral skin of each rabbit ear in a sterile environment.

After 21 d of modeling, a raised, dark red, hard, and thickened scar tissue was formed on the healing site of the original surface, indicating that the scar model was successfully constructed. The engineered exosome treatment group underwent subcutaneous injection of the engineered exosome miR-141-$3p^{OE}$-Exos at 4 points (0 o'clock, 3 o'clock, 6 o'clock, and 9 o'clock directions) around the wound every week for a total of 100 μL, 25 μL per point, for a total of 3 weeks. The control group used the same injection method, and the exosomes were replaced by miR-141-$3p^{NC}$-Exos.

The scar condition was observed every day after treatment, and the rabbits were euthanized and the scar tissue was removed one week after each treatment. The scar tissue was fixated in paraformaldehyde and made into paraffin tissue sections, and tissue staining was conducted to evaluate the condition of HTS.

Figure 5:
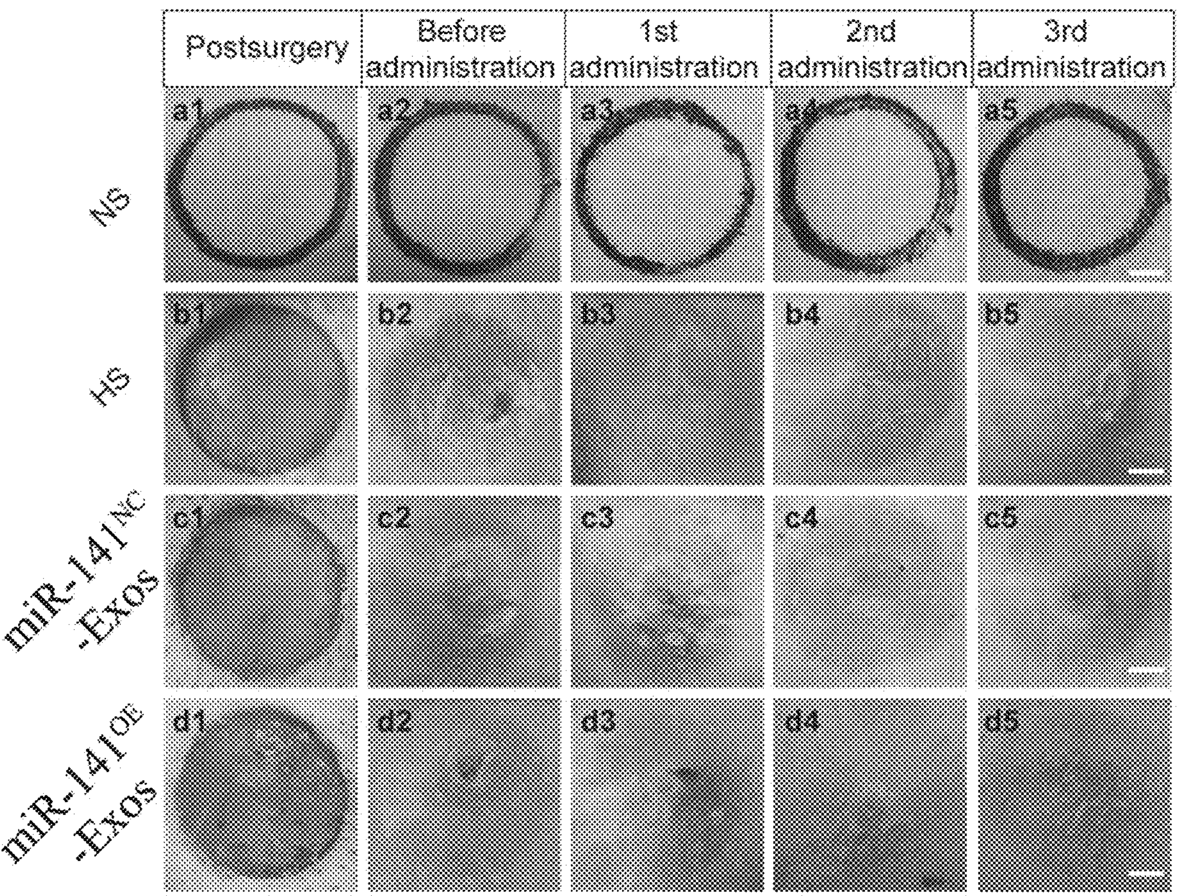
FIG. 5 shows images of the HTS on rabbit ears provided in Example 3 of the present disclosure.
Figure 6:
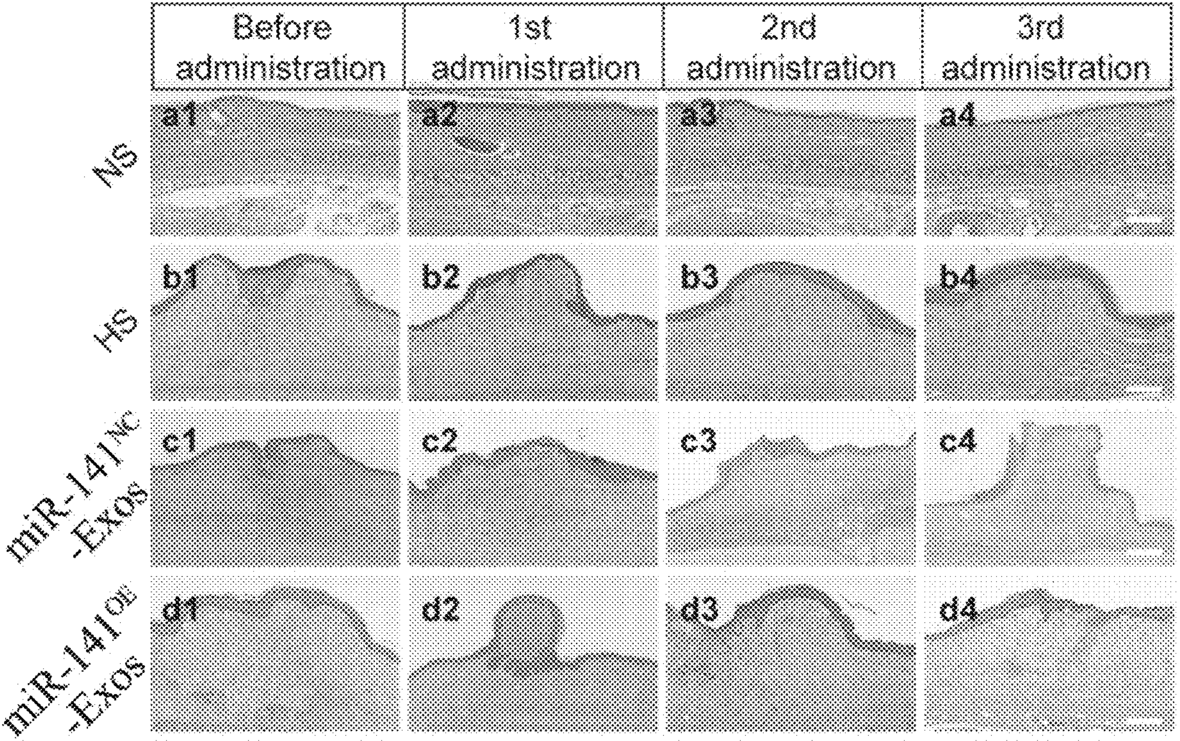
FIG. 6 shows the H&E staining of each group of wound tissues provided in Example 3 of the present disclosure.

The results of the evaluation and analysis of the effect of using engineered MSC-derived exosomes to treat rabbit ear HTS model were shown in FIG. 5 and FIG. 6. FIG. 5 was a picture of rabbit ear HTS, and FIG. 6 was a picture of H&E staining of wound tissue in each group. As shown in FIG. 5, on day 21 after surgery, all wounds were completely epithelialized, and rabbit ear HTS with a raised and dark red appearance was successfully constructed. Compared with the miR-141-$3p^{NC}$-Exos group, the surface of the scar tissue in the miR-141-$3p^{OE}$-Exos treatment group was flatter and lighter in color after three administrations.

H&E staining was shown in FIG. 6. After scar formation, the miR-141-3p$^{OE}$-Exos group showed flatter dermis and more aligned fibroblasts than the miR-141-3p$^{NC}$-Exos group. Combining the results in FIG. 5 and FIG. 6, the miR-141-3p$^{OE}$-Exos group had a superior function of inhibiting HTS than that of the miR-141-3p$^{NC}$-Exos group.

Although the above example has described the present disclosure in detail, it is only a part of, not all of, the examples of the present disclosure. Other examples may also be obtained by persons based on the example without creative efforts, and all of these examples shall fall within the protection scope of the present disclosure.

What is claimed is:

1. An engineered exosome for treating hypertrophic scar (HTS), wherein the engineered exosome is a mesenchymal stem cell (MSC)-derived exosome expressing miR-141-3p;

wherein the engineered exosome is prepared by a process comprising the following steps:

(1) infecting an MSC with a miR-141-3p-expressing lentivirus, and conducting screening to obtain a stably transduced cell line; and (2) subjecting the stably transfected cell line to multiplication culture, and conducting exosome extraction to obtain the engineered exosome for treating HTS;

wherein in step (1), the miR-141-3p-expression lentivirus is packaged by an LV3 vector, the infecting is conducted for 20 h to 24 h, and the screening comprises screening a successfully transfected MSC with puromycin; and wherein in step (2), a medium for the multiplication culture comprises a serum-free medium for the MSC.

2. A method for preparing an engineered exosome, comprising the following steps:

(1) infecting an MSC with a miR-141-3p-expressing lentivirus, and conducting screening to obtain a stably transduced cell line; and (2) subjecting the stably transfected cell line to multiplication culture, and conducting exosome extraction to obtain the engineered exosome for treating HTS, wherein in step (1), the miR-141-3p-expression lentivirus is packaged by an LV3 vector, the infecting is conducted for 20 h to 24 h, and the screening comprises screening a successfully transfected MSC with puromycin; and wherein in step (2), a medium for the multiplication culture comprises a serum-free medium for the MSC.

3. The method according to claim 2, wherein a process of the exosome extraction comprises the following steps:

collecting a cell supernatant obtained from the multiplication culture;

subjecting the cell supernatant to low-speed centrifugation;

collecting a resulting supernatant to allow filtration with an ultrafiltration membrane;

subjecting a resulting filtrate to ultracentrifugation; and collecting a resulting precipitate to obtain the engineered exosome for treating HTS.

4. The method according to claim 3, wherein the low-speed centrifugation is conducted at 2,000 g for 10 min; and the ultrafiltration membrane has a pore size of 0.22 μm.

5. The method according to claim 3, wherein the ultracentrifugation is conducted at 100,000 g for 75 min.

6. A method for treating HTS, comprising administering the engineered exosome for treating HTS according to claim 1 to a patient in need thereof.

* * * * *